United States Patent [19]

Murray et al.

[11] Patent Number: 4,639,372

[45] Date of Patent: Jan. 27, 1987

[54] COCCIDIOSIS VACCINE

[75] Inventors: Peter K. Murray, Redbank; Stefan Galuska, North Plainfield, both of N.J.

[73] Assignee: Merck & Co., Inc., Rahway, N.J.

[21] Appl. No.: 625,882

[22] Filed: Jun. 29, 1984

[51] Int. Cl.$^4$ .................. A61K 39/012; A61K 37/00
[52] U.S. Cl. ..................... 424/88; 530/403; 514/2
[58] Field of Search .............. 260/112 R; 424/88; 514/2; 530/403

[56]  References Cited

PUBLICATIONS

Statish, R. et al., J. Biol. Chem., vol. 251, pp. 302–307.
Rose et al., Symposium of the British Society for Porasitology, vol. 18, pp. 57–74, 1980.

Primary Examiner—Blondel Hazel
Attorney, Agent, or Firm—Donald J. Perrella; Hesna J. Pfeiffer

[57] ABSTRACT

Sporozoites of coccidia fail to develop in chickens which are immune and many are blocked from penetrating host cells. Although previous attempts to immunize chickens with non-viable coccidial antigens have been unsuccessful it has been discovered that extracts from sporozoites or sporulated oocysts of E. tennella induce high levels of protective immunity. These extracts contain at least 15 polypeptides many of which are associated with the surface of the sporozoite and induce good immune responses. Antibody to these polypeptides blocks sporozoite-host cell penetration in vitro and neutralizes sporozoites in vivo. One or more of these polypeptides may be used as an antigen to protect against coccidiosis.

13 Claims, No Drawings

COCCIDIOSIS VACCINE

BACKGROUND OF THE INVENTION

Coccidiosis refers to the disease condition caused by infection with one or more of the many species of coccidia, a subdivision of the phylum Protozoa. The genus Eimeria contains the species of major economic importance in domestic birds. While coccidiosis occurs in practically all kinds of birds, the parasites are host specific and each species occurs in a single or in a limited group of related hosts. On the other hand, avian hosts are known to harbor more than one species of coccidia. The two most important species from the aspect of economic loss are *E. tenella* and *E. acervulina*. Additional important species in chickens include *E. maxima*, *E. necatrix*, *E. mivati* and *E. brunetti* with *E. mitis*, *E. praecox* and *E. hagani* causing infections of lesser importance.

Other types of livestock, e.g., cattle, sheep, goats and pigs also can suffer severely from coccidiosis with resultant loss of productivity.

Among domesticated birds, chickens are the most susceptible to significant economic losses from coccidiosis, although losses can also occur within turkeys, geese, ducks, and guinea fowl. Coccidiosis has also produced serious losses in pheasants and quail raised in captivity. The effects of a coccidiosis infection can take the highly visible form of devastating flock mortality, but another undesirable effect is morbidity and/or weight loss which results from infection.

When chickens recover from infection with coccidia they generally are immune. However, all prior efforts to vaccinate poultry against coccidiosis using non-living extracts of *Eimeria* have met with failure.

OBJECTS OF THE INVENTION

It is, accordingly, an object of the present invention to provide an extract of parasite antigens which protects against coccidiosis. Another object is to provide immunogenic polypeptides of the type normally located on the surface of the intact sporozoite. Another object is to provide means for obtaining these immunogenic extracts and antigens. Another object is to provide compositions for prophylactic administration of these antigens. A further object is to provide a coccidiosis vaccine which is protective against those forms of Eimeria mainly responsible for economic loss. These and other objects of the present invention will be apparent from the following description.

SUMMARY OF THE INVENTION

Extracts from the sporulated oocyst and sporozoite stages of *Eimeria tenella* have been prepared and used to immunize chickens. These chickens have become protected against the morbidity and mortality caused by virulent *E. tenella* infection. Extracts from the sporulated oocyst were prepared by grinding this stage and collecting the supernatant (PGS) followed by sonication and freeze-thawing. Extracts of sporozoites were prepared by freeze-thawing and sonication of DEAE anion exchange purified sporozoites. Immunization with these extracts protected chickens against coccidiosis caused by *E. tenella*. The extracts contain both polypeptides and lipids. Of the 15 important polypeptides, i.e., the <10, 10, 15, 19, 23, 26, 40, 45, 50, 68, 82, 94, 105, 235 and 330 KD molecules, nine are associated with the surface of the sporozoite and one or a combination of these can induce good immune responses to the sporozoite. Antibody to these and other sporozoite polypeptides blocks sporozoite penetration and development in vitro and neutralizes sporozoite infectivity in vivo. One or more of these polypeptides may be used as an antigen to prophylactically immunize against coccidiosis.

DETAILED DESCRIPTION OF THE INVENTION

The present invention relates to a coccidiosis vaccine based on parasite extracts containing lipids and one or more immunogenic polypeptides normally found on the surface of the intact sporozoite, to the immunogenic polypeptides themselves, to methods of obtaining these extracts or immunogenic polypeptides, and to the use of the extracts or the immunogenic polypeptides in preparing a vaccine effective against coccidiosis.

Sporozoites represent a likely target for a protective immune response since in immune chickens they undergo a very restricted development or may even fail to penetrate cells in the intestinal tract. Thus the immune block of the sporozoite-host cell interaction is proposed as one objective of vaccination.

Parasite extracts are obtained from (1) sporulated oocysts and/or, (2) sporozoites. Post-grind supernatant fluid (PGS) is obtained from sporulated oocysts after grinding this stage and collecting the supernatant by centrifugation. Sporozoites are obtained by subjecting the pelleted parasite materials, derived from sporulated oocysts after grinding and centrifugation, to an excysting solution, then centrifugation and anion exchange column chromatography.

Polypeptides are obtained for analysis by the separation of sporozoite or PGS antigens by sodium dodecyl sulfate polyacrylamide gel electrophoresis. Polypeptides are also obtained by immunoaffinity purification of antigens contained in PGS and sporozoites using monoclonal anti-*E. tenella* sporozoite antibody coupled to agarose, e.g., Sepharose Cl-4B. In addition, polypeptides are obtained by solubilization of membrane proteins of intact sporozoites using detergents, for example, octylphenoxy polyethoxy (9) ethanol, ethylphenyl-polyethyleneglycol, N-dodecyl-N,N-dimethyl-3-ammonio-1-propanesulfonate, deoxycholate or octyl glucoside. PGS and sporozoites are also separated into their component polypeptides on a gel filtration column, e.g., Sephacryl S 200.

There are nine immunogenic polypeptides which are components of PGS and sporozoites which are associated with the surface of sporozoites. These are polypeptide antigens of 23, 26, 40, 45, 68, 82, 94, 105 and 235 KD molecular weight which are capable either singly or in combination of inducing immune responses in chickens which protect them against coccidiosis. In addition, polypeptides of <10, 10, 15, 19, 50, and 330 KD are immunogenic and play an important role in the sporozoite since antibodies to these materials block the penetration of sporozoites into host cells.

Chickens are immunized by inoculating the antigens listed above either singly or in combination or as a parasite extract. Immunization by the oral, intramuscular or cloacal route with these antigens results in chickens developing immunity to infection such that after exposure to virulent parasites no significant disease results. Protective immunity is achieved by administering from about 1 to about 200 μg of antigen per chicken on from 1 to 4 separate occasions.

The following examples illustrate the present invention without, however, limiting the same thereto.

EXAMPLE 1

Preparation of Parasite Materials

Oocysts—Cecal cores (coalesced massed of oocysts) of *Eimeria tenella* (Merck strain LS18) isolated from chickens infected 7 days earlier were disrupted in a Waring Blender (in distilled water) and digested with pepsin (2 mg/ml) at pH 2.0 and 39° C. for 1 hour. Large amounts of debris and the pepsin were removed from pelleted material after centrifugation (1,000 xg) in distilled water. A partially pure oocyst fraction was isolated from the pellet by flotation in 2.2M sucrose (Jackson, Parasitol. 54: 87–93, 1964) and this crude material further treated by incubating in cold Clorox (5.25% sodium hypochlorite, 4° C.) for 10 minutes. The sodium hypochlorite was removed by several washes in sterile phosphate-buffered saline (PBS) pH 7.6 to obtain purified and sterile oocysts.

Sporulated Oocysts—Oocysts prepared as above were sporulated in a shaking water bath at 29° C. for 48 hours (Edgar, Trans, Am. Micr. Soc. 62: 237–242, 1954). Sporulated oocysts were stored in PBS (pH 7.6) at 4° C. until use.

Post-grind Supernatant—A 2 ml suspension of purified sporulated oocysts ($5 \times 10^7$/ml PBS, pH 7.6) was ground at 500 rpm for 5 minutes at 4° C. in a tissue homogenizer with a loose-fitting pestle (Patton, Science 150: 767–769, 1965) and the supernatant material resulting from the disruption of the oocysts was removed after centrifugation (2,000 rpm $\times$ 10 minutes). This milky, lipid-rich material was designated post-grind supernatant (PGS). Pelleted material was further processed for sporozoites.

PGS was subjected to sodium dodecyl sulfate polyacrylamide gel electrophoresis (SDS-PAGE) to separate the polypeptides. Thirteen polypeptides were prominent, staining strongly with Coomassie blue. These were 235, 175, 105, 94, 88, 82, 80, 68, 60, 50, 45, 28 and 26 KD dalton polypeptides. In addition, seven polypeptides reacted strongly with anti-sporozoite sera in Western blot analyses. These were 235, 105, 94, 71, 64, 45 and 26 KD molecular weight. This indicates these proteins are strong antigens.

A lipid fraction of the PGS was prepared by chloroform:methanol (1:1) extraction and analyzed by thin layer chromatography (TLC). About 5–10 µl of the lipid mixture, dissolved in the foregoing solvent mixture, were spotted on a silica-coated TLC plate and chromatographed using methanol as solvent. Three different stains were used to identify the components: iodine for lipids, ninhydrin for peptides and anisaldehyde for carbohydrates. Exposure to iodine vapor gave two intense yellow spots, one above the origin and the other moving slightly behind the solvent front; the latter was a large spot comprising three lipid components. All these lipid spots could be stained with anisaldehyde; thus, they were glycolipids. Between these glycolipids were 4 well resolved ninhydrin positive peptide spots. The fastest moving peptide showed a weak color with iodine vapor suggesting the presence of a peptide-linked lipid. The origin was clear of any spot after chromatography.

EXAMPLE 2

Preparation of Sporozoite Antigen (SA)

Sporozoites—The pelleted material obtained in Example 1, composed of unbroken oocysts, sporozoites, and oocyst shells, was resuspended in an excysting solution containing 0.25% (w/v) trypsin (1:250) and 4.0% (w/v) taurodeoxycholic acid (Sigma, St. Louis, MO) in Hanks balanced salt solution (pH 7.4) and incubated at 41° C. in 5% $CO_2$ (Patton et al., J. Parasitol. 65: 526–530, 1979). After 1 hour, the excysting solution was removed by centrifugation and parasite material was washed twice in phosphate buffered saline glucose (PBSG) (2:8 PBS; H20 v/v) buffer of pH 8.0, ionic strength 0.145 containing 1% glucose (Schmatz et al., J. Protozool. 31: 181–183, 1984). The parasite mixture was applied to a DE52 anion exchange column, equilibrated in PBSG and sporozoites, purified from other parasite materials, were eluted unretarded in the void volume (Schmatz et al., supra).

Sporozoites were freeze thawed 3 times (dry ice to room temperature and sonicated until disrupted in PBS with 1 mM phenylmethylsulfonylfluoride as protease inhibitor to provide sporozoite antigen (SA). Protein concentrations were determined by the method of Lowry et al., J. Biol. Chem. 193: 265–275, 1951 and antigens were stored in liquid $N_2$.

The polypeptides of sporozoites were analyzed according to the table shown below. The findings show the nine polypeptides that are located on the surface of the sporozoite and that seven of these are capable of inducing good antibody responses as indicated by their reactivity in western blots with anti-sporozoite antibody.

| Number of Bands | Molecular Weight (KD) | | | | | | | | | | | Technique |
|---|---|---|---|---|---|---|---|---|---|---|---|---|
| 11 | 235 | 175 | 105 | 94 | 82 | | | 60 | 50 | 45 | 28 | 23 | SDS-PAGE Coomassie. Strongly stained. |
| 9 | 235 | | 105 | 94 | 82 | 71 | 68 | 64 | | 45 | | 26 | | Western blot, R anti-sporozoite. |
| 3 | | | | | | | | | | 45 | | 26 | <15 | $I^{125}$ surface label |
| 9 | 235 | | 105 | 94 | 82 | | 68 | | | 45 | 40 | 26 | 23 | Zwittgerent membrane solubilization. Conclusion |
| 7 | 235 | | 105 | 94 | 82 | | 68 | | | 45 | | 26 | | Immunogenic surface. Sporozoite polypeptides. |

The lipid fraction profile of sporozoites was virtually identical to that of Example 1 except that there were four peptides appearing as a streak and these were small amounts of material at the origin staining for both lipids and a peptide.

EXAMPLE 3

Immunization of Chickens Against Coccidiosis With an Extract of Sporulated Oocysts (PGS)

Post-grind supernatant (PGS) was prepared as detailed in Example 1 and freeze-thawed by rapid cooling to dry ice temperature followed by rapid warming to room temperature three times. Subsequently the PGS was sonicated in phosphate buffered saline containing 1 mM phenylmethylsulfonylfluoride to inhibit protein degradation. Male outbred broiler chickens (Hubbard Farms) aged three weeks were immunized by different routes of inoculation with PGS containing 50 mcg protein as determined by the method of Lowry et al., supra. Immunizations were carried out once weekly. Two weeks after the last immunization an oral inoculation of $1.7 \times 10^5$ fully virulent E. tenella sporulated oocysts (prepared as detailed in Example 1) was administered. The experimental broiler chickens were sacrificed six days after this inoculation and the severity of lesions in the ceca of these chickens determined according to a defined scale of 1 to 4 where 4 is the most severe. (In E. tenella infection in chickens the ceca are the preferred site of parasite multiplication and pathological changes occur particularly at these sites.)

The results are shown below.

| | Immunization of Chickens with PGS | | | |
|---|---|---|---|---|
| | Immunization | | | % Positive[2] |
| Group | Route | Frequency | n[1] | Lesion Scores |
| 1 | Intramuscular | Weekly × 4 | (5) | 0 |
| 2 | Per Cloaca | Weekly × 4 | (4) | 25 |
| 3 | Intravenous | Weekly × 6 | (5) | 60 |
| 4 | None | — | (11) | 91 |

[1]Number of chickens per group
[2]Scores >1
Mean lesion scores in group 1 were 0 out of a possible maximum of 4.0.
Mean lesion scores in group 2 were 0.75 out of a possible maximum of 4.0.
Mean lesion scores in group 3 were 2.4 out of a possible maximum of 4.0.
Mean lesion scores in group 4 were 2.7 out of a possible maximum of 4.0.

These results show that PGS, an extract from E. tenella sporulated oocysts which contains no viable or intact parasites, can be used to immunize chickens when given by intramuscular, per-cloaca or intravenous inoculation and provides a high level of protection against the disease as indicated by the absence of lesions developing in immune birds after a normally virulent infection.

EXAMPLE 4

Oral Immunization of Chickens Against Coccidiosis With an Extract of Sporulated Oocysts (PGS)

Post-grind supernatant (PGS) was prepared for inoculation as detailed in Example 3. As in that example, male outbred broiler chickens aged three weeks were used. These were immunized by the inoculation of PGS weekly on four occasions per os according to the table below. One week after the last immunization, chickens were inoculated with $1 \times 10^4$ fully virulent E. tenella sporulated oocysts (prepared as detailed in Example 1). The experimental chickens were sacrificed seven days after this inoculation and the severity of lesions in the ceca of these chickens was determined as in the previous example. In addition, the numbers of oocysts in the feces was determined by hemocytometer counts of material derived by salt flotation according to a standard technique.

The results are shown below.

| | Immunization of Chickens with PGS | | | | |
|---|---|---|---|---|---|
| | Immunization | | | % Positive[2] | Oocyst |
| Group | Route | Dose | n[1] | Lesion Scores | Counts |
| 1 | oral | 100 mcg | 5 | 0 | <10[4] |
| 2 | oral | 50 mcg | 5 | 20 | <10[4] |
| 3 | oral | 25 mcg | 5 | 40 | 10[5] |
| 4 | oral | 10 mcg | 5 | 100 | 4 × 10[6] |

[1]number of chickens per group
[2]Scores >1
Mean lesion scores in group 1 were 0.2 out of a possible maximum of 4.
Mean lesion scores in group 2 were 0.8 out of a possible maximum of 4.
Mean lesion scores in group 3 were 1.7 out of a possible maximum of 4.
Mean lesion scores in group 4 were 2.4 out of a possible maximum of 4.

These results show that PGS, an extract from E. tenella sporulated oocysts, which contains no viable or intact parasites, can be used to immunize chickens when given by the per-oral route of inoculation and provides a high level of protection against the disease as indicated by the absence of lesions and the reduction in oocysts developing in immune birds after a normally virulent infection.

EXAMPLE 5

Immunization of Chickens Against Coccidiosis With an Extract of Sporozoites

Sporozoites were prepared as detailed in Example 2 and freeze-thawed by rapid cooling to dry ice temperature followed by rapid warming to room temperature three times. Subsequently the sporozoite antigen was sonicated in phosphate buffered saline containing 1 mM phenylmethylsulfonylfluoride to inhibit protein degradation. Male outbred broiler chickens (Hubbard Farms) aged three weeks were immunized by inoculation with sporozoite antigen containing 100 mcg of protein as determined by the method of Lowry et al., supra, weekly as shown in the table below. Two weeks after the last immunization an oral inoculation of $1 \times 10^4$ fully virulent E. tenella sporulated oocysts (prepared as detailed in Example 1) was administered. Chickens were sacrificed 6 days after this inoculation and the severity of lesions in the ceca of these chickens determined as in Example 4. In addition, the numbers of oocysts in the feces was determined by hemocytometer counts of material derived by salt flotation according to a standard technique.

The results are shown below.

| | Immunization of Chickens Against Coccidiosis With an Extract of Sporozoites | | | | |
|---|---|---|---|---|---|
| | Immunization | | | % Positive[2] Lesion | Oocyst |
| Group | Route | Frequency | n[1] | Scores | Counts |
| 1 | Intramuscular | Weekly × 2 | 6 | 0 | <10[4] |
| 2 | Intramuscular | Weekly × 3 | 6 | 0 | <10[4] |
| 3 | Intramuscular | Weekly × 4 | 6 | 17 | <10[4] |
| 4 | None | — | 17 | 83 | 7 × 10[6] |

[1]Number of chickens per group.
[2]Scores >1.
Mean lesion scores in group 1 were 0.4 out of a possible maximum of 4.0.
Mean lesion scores in group 2 were 0.2 out of a possible maximum of 4.0.
Mean lesion scores in group 3 were 0.6 out of a possible maximum of 4.0.
Mean lesion scores in group 4 were 1.9 out of a possible maximum of 4.0.

These results show that sporozoite antigen, an extract from purified E. tenella sporozoites which contains no viable or intact parasites, can be used to immunize chickens when given by the intramuscular route of inoculation and provides a high level of protection against the disease as indicated by the absence of lesions and the reduction in oocysts developing in immune birds after a normally virulent infection.

defined. These results of investigation of some selected monoclonals are shown below.

| The Reactivity of Monoclonal Antibodies with E. tenella Sporozoites | | | | | | |
|---|---|---|---|---|---|---|
| Monoclonal Antibody Number | Isotype | Agglutination[1] | Indirect/[2] IFA | Penetration/[3] Development Inhibition | In vivo[4] Neutralization | Reactive[5] Sporozoite Polypeptides M wt (KD) |
| 15-1 | IgG | − | ND | + | + | 82 |
| 326-10 | IgG | − | + | − | + | 105,94 |
| 363-5 | IgG | − | − | + | ND | None |
| 1025-12 | IgG | + | + | + | + | None |
| 1041-1 | IgG1 | + | + | + | + | None |
| 1073-10 | IgG3 | + | + | ± | + | 68 |
| 1096-9 | IgG3 | + | + | ± | ± | 105,82 |
| 1133-8 | IgM | − | + | ± | + | None |
| 1156-2 | IgG3 | + | ND | + | ND | ND |
| 1378-5 | IgG1 | − | + | ± | + | 26,28 |
| 1495 | IgM | − | + | ND | ND | 330,26 |
| 1546-4 | IgG | − | + | − | ND | 50,45,26,19,15,10,10 |
| 1569 | IgG | + | + | − | + | 50 |
| 1797-5 | IgG1 | − | + | − | + | 105 |

[1]Agglutination of purified E. tenella sporozoites.
[2]Indirect immunofluorescence of acetone-fixed purified E. tenella sporozoites using fluorescein conjugated rabbit anti-mouse Ig.
[3]Inhibition of purified E. tenella sporozoite penetration and early development in cloned MOBK monolayer cultures using radiolabelled uracil as a marker for parasite specific growth.
[4]The neutralization of purified E. tenella sporozoites. Sporozoites were reacted with antibody in vitro then inoculated, per cloaca, into the cecal region of chickens. Lesion scores and oocyst counts were determined 6 days later.
[5]Western blot analyses using sporozoite antigen on SDS-PAGE separated sporozoite polypeptides transferred to nitrocellulose paper.
[6]ND = Not determined.

EXAMPLE 6

Important Coccidiosis Vaccine Polypeptides Defined by Monoclonal Antibodies

Hybridomas producing monoclonal antibodies to intact E. tenella sporozoites were made in mice in a similar manner to those made by Danforth (J. Parasitol 68: 392–397, 1982). Cell lines producing anti-sporozoite antibodies were identified by solid phase radioimmunoassay against purified sporozoite antigen. Monoclonal antibodies were purified from these hybridomas by growing each cell line in tissue culture in 200 ml media, separating the hybridoma supernatant material by centrifugation, concentration of the protein in this supernatant by ultrafiltration (Hanna Biologics Inc.: Purification of monoclonal antibodies produced in mB101 ™ serum-free medium, C.E. Chandler, L.M. Parsons) or, precipitation of protein with 50% ammonium sulfate. Antibody was purified from this concentrate by affinity column chromatography with protein A - Sepharose CL4B or with anti IgG, IgA or IgM attached to Sepharose 4B according to the procedures outlined in Pharmacia Fine Chemicals, Affinity chromatography: Principles and Methods.

Purified monoclonal antibodies to E. tenella sporozoites were assayed for their biological effects, i.e., their ability to agglutinate intact sporozoites, their ability to react with sporozoites by indirect immunofluorescence assays, their ability to affect penetration and/or development of sporozoites in host cells in a newly developed tissue culture assay system and their ability to neutralize the infectivity of sporozoites given per cloacally into the cecal region of individual chickens. In addition, the individual sporozoite polypeptides which react with these monoclonals were determined by Western blot analysis of sporozoite antigens.

As a result of these analyses, the importance of individual sporozoite polypeptides as vaccine antigens was defined. These findings show that polypeptides of molecular weights <10, 10, 15, 19, 26, 45, 50, 68, 82, 94, 105 and 330 KD are of critical function in the sporozoite since monoclonals which react with these polypeptides exert important effects on the parasite i.e., this interaction can result in one or all of the following: specific attachment of antibody to the parasite (demonstrated by positive indirect immunofluorescence), in agglutination of the parasite (demonstrated by positive agglutination assay), in the blocking of sporozoites from penetrating host cells (demonstrated by positive penetration/development inhibition assay), and, most importantly, in the blocking of the ability of the sporozoite to infect chickens.

Thus, the individual sporozoite polypeptides listed above are important to be included in the vaccine either alone or in combination since the immune response of the chicken to these antigens has important blocking effects on sporozoite penetration and development thus protecting the chicken from disease.

What is claimed is:

1. An extract obtained by grinding and centrifuging a suspension of sporulated oocysts of Eimeria tenella, and purifying sporozoites from the pelleted material resulting from the centrifugation step, the pelleted material containing antigens capable of immunizing chickens against coccidiosis.

2. An extract from the supernatant liquid obtained by centrifuging a suspension of ground sporulated oocysts of Eimeria tenella, the extract containing polypeptides having molecular weights of 235, 105, 94, 71, 64, 45 and 26 KD.

3. An extract of the pelleted material of claim 1 having immunogenic polypeptides containing molecular weights of 235, 105, 94, 82, 68, 45, 40, 26 and 23 KD.

4. An extract of the pellleted material of claim 1 containing immunogenic polypeptides of 10, 10, 15, 19, 26, 28, 45, 50, 68, 82, 94, 105 and 330 KD against which monoclonal antibodies specific to Eimeria tenella react.

5. A method of immunizing chickens against coccidiosis comprising administering an anti-coccidial effective dose of the extract of claim 2.

6. A method of immunizing chickens against coccidiosis comprising administering an anti-coccidial effective dose of the extract of claim 1.

7. A method of immunizing chickens against coccidiosis comprising administering an anti-coccidial effective dose of the immunogenic polypeptides of claim 2.

8. A method of immunizing chickens against coccidiosis comprising administering an anti-coccidial effective dose of the immunogenic polypeptides of claim 3.

9. A method of immunizing chickens against coccidiosis comprising administering an anti-coccidiosis effective dose of the immunogenic polypepcoccidial tides of claim 4.

10. An anti-coccidial composition comprising an anti-coccidial effective amount of the extract of claim 1 in a physiologically acceptable medium.

11. An anti-coccidial composition comprising an anti-coccidial effective amount of the extract of claim 2 in a physiologically acceptable medium.

12. An anti-coccidial composition comprising an anti-coccidial effective amount of the extract of claim 4 in a physiologically acceptable medium.

13. An anti-coccidial composition comprising an anti-coccidial effective amount of the extract of claim 4 in a physiologically acceptable medium.

* * * * *